(12) United States Patent
Umezawa et al.

(10) Patent No.: US 6,963,630 B2
(45) Date of Patent: Nov. 8, 2005

(54) METHOD FOR EVALUATING AN SOI SUBSTRATE, EVALUATION PROCESSOR, AND METHOD FOR MANUFACTURING A SEMICONDUCTOR DEVICE

(75) Inventors: Kaori Umezawa, Kanagawa-ken (JP); Norihiko Tsuchiya, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 23 days.

(21) Appl. No.: 10/336,685

(22) Filed: Jan. 6, 2003

(65) Prior Publication Data
US 2003/0128809 A1    Jul. 10, 2003

(30) Foreign Application Priority Data
Jan. 7, 2002   (JP)   ............ P 2002-000215

(51) Int. Cl.$^7$ ........................... G01N 23/207
(52) U.S. Cl. ........................ 378/74; 378/71
(58) Field of Search ............ 378/70, 71, 73, 378/74, 76, 77

(56) References Cited

U.S. PATENT DOCUMENTS 5,461,007 A * 10/1995 Kobayashi ............ 438/16
6,064,717 A * 5/2000 Ortega et al. ........... 378/71
6,385,289 B1 * 5/2002 Kikuchi ................. 378/79
6,537,606 B2 * 3/2003 Allen et al. ............. 427/9
2001/0043668 A1 * 11/2001 Hayashi et al. .......... 378/89

FOREIGN PATENT DOCUMENTS

JP    9-311111    12/1997

* cited by examiner

Primary Examiner—Edward J. Glick
Assistant Examiner—Chih-Cheng Glen Kao
(74) Attorney, Agent, or Firm—Finnegan, Henderson, Farabow, Garrett & Dunner, L.L.P.

(57) ABSTRACT

A method for evaluating an SOI layer on an insulating film disposed on a base substrate so as to construct an SOI substrate, includes: measuring a first diffraction intensity distribution of an X-ray beam corresponding to an incident angle formed with the X-ray beam and a front surface of the SOI substrate by irradiating the X-ray beam onto the base substrate; measuring a second diffraction intensity distribution of the X-ray beam for the incident angle formed with the X-ray beam and the front surface of the SOI substrate by irradiating the X-ray beam onto the SOI layer; determining an evaluation diffraction peak corresponding to the SOI layer from the first and the second diffraction intensity distribution; and observing an X-ray topograph by irradiating the X-ray beam on the SOI layer with a second incident beam angle of the evaluation diffraction peak.

16 Claims, 10 Drawing Sheets

METHOD FOR EVALUATING AN SOI SUBSTRATE, EVALUATION PROCESSOR, AND METHOD FOR MANUFACTURING A SEMICONDUCTOR DEVICE

CROSS REFERENCE TO RELATED APPLICATIONS

This application is based upon and claims the benefit of priority from prior Japanese Patent Application P2002-215 filed on Jan. 7, 2002; the entire contents of which are incorporated herein by reference.

BACKGROUND OF THE INVENTION

1. Field of the Invention

The present invention relates to an evaluation method for a silicon on insulator (SOI) substrate. In particular, it relates to a method for evaluating crystallographic properties of an SOI layer (semiconductor layer) on the base substrate of the bonded SOI substrate, and an evaluation processor for implementing this method.

2. Description of the Related Art

In an SOI substrate used in semiconductor device manufacturing, an SOI layer served as a semiconductor layer, such as a silicon (Si) layer, is provided on an insulating substrate such as a sapphire substrate, or on an insulating film on a semiconductor substrate. A bonded SOI substrate is prepared by bonding the SOI layer above a base substrate, so that the SOI layer being in contact with an insulating film such as a silicon oxide ($SiO_2$) film formed on the base substrate. In the bonded SOI substrate, the SOI layer is used as an active region of a semiconductor device. Even if some crystal defects are introduced in the base substrate, the semiconductor device fabricated in the SOI layer disposed above the base substrate may still perform many functions. However, if a significant amount or number of crystal defects are introduced in the SOI layer serving as the active region of the semiconductor device, the semiconductor device may not sufficiently perform required functions.

For example, slip dislocations may possibly be induced in the SOI substrate due to an annealing procedure conducted during manufacture of the bonded SOI substrate. In manufacturing processes of a semiconductor device using the bonded SOI substrate, when the slip dislocations occur in the SOI layer, serving as the active region of the semiconductor device, a slight amount of heavy metals contained in the SOI substrate may be diffused into the SOI layer and trapped in the slip dislocations, due to thermal processing included in the manufacturing processes. The slip dislocations which trap the heavy metals in the active region of the semiconductor device may cause performance and operation problems of the semiconductor device, such as causing an excessive leakage current. On the other hand, as mentioned above, the slip dislocations induced in the base substrate may not produce a substantial affect on the operation of the semiconductor device. Accordingly, evaluation of the crystallographic quality of the SOI layer is an indispensable process for effectively manufacturing the semiconductor device. In addition, determination of whether crystal defects such as the slip dislocations have been created in the base substrate or the SOI layer of the SOI substrate is extremely important for manufacturing the semiconductor device.

X-ray topography is known as a method for evaluating crystal defects in a single crystal substrate, for example a Si substrate. Observation of the X-ray topography may allow evaluation of the crystal defects across the entire area of a large diameter semiconductor substrate. Accordingly, in comparison with evaluation methods using selective etching or transmission electron microscopy (TEM), non-destructive observation of crystal defects may be easily performed over a wider evaluation range.

In the bonded SOI substrate, crystal orientation between the SOI layer and the base substrate usually do not match. Accordingly, when observing the bonded SOI substrate by X-ray topography, the crystal defects in the base substrate may be evaluated, but those in the SOI layer cannot be evaluated appropriately.

SUMMARY OF THE INVENTION

A first aspect of the present invention inheres in a method for evaluating an SOI layer on an insulating film disposed on a base substrate so as to construct an SOI substrate and includes: measuring a first diffraction intensity distribution of an X-ray beam corresponding to an incident angle formed with the X-ray beam and a front surface of the SOI substrate by irradiating the X-ray beam onto the base substrate; measuring a second diffraction intensity distribution of the X-ray beam for the incident angle formed with the X-ray beam and the front surface of the SOI substrate by irradiating the X-ray beam onto the SOI layer; determining an evaluation diffraction peak corresponding to the SOI layer from the first and the second diffraction intensity distribution; and observing an X-ray topograph by irradiating the X-ray beam on the SOI layer with a second incident beam angle of the evaluation diffraction peak.

A second aspect of the present invention inheres in a evaluation processor for an SOI layer on an insulating film disposed on a base substrate so as to construct an SOI substrate and includes: an X-ray topography apparatus; a data input module configured to receive X-ray beam diffraction intensity data corresponding to the base substrate and the SOI layer measured by the X-ray topography apparatus; an angle analysis module configured to analyze an incident beam angle of a diffraction intensity peak from the diffraction intensity data distribution; an angle determination module configured to determine a first incident beam angle corresponding to the base substrate, and a second incident beam angle corresponding to the SOI layer from the analyzed incident beam angle; and a data output module configured to output the first and second incident beam angles to the X-ray topography apparatus.

A third aspect of the present invention inheres in a method for manufacturing a semiconductor device and includes: forming an SOI layer on an insulating film disposed on a base substrate so as to construct an SOI substrate; performing a manufacturing process for a semiconductor device on the SOI layer; observing an X-ray topograph of the SOI layer treated by the manufacturing process, comprising: measuring a first diffraction intensity distribution of an X-ray beam corresponding to an incident angle formed with the X-ray beam and a front surface of the SOI substrate by irradiating the X-ray beam onto the base substrate; measuring a second diffraction intensity distribution of the X-ray beam for the incident angle formed with the X-ray beam and the front surface of the SOI substrate by irradiating the X-ray beam onto the SOI layer; determining an evaluation diffraction peak corresponding to the SOI layer from the first and the second diffraction intensity distribution; and observing an X-ray topograph by irradiating the X-ray beam on the SOI layer with a second incident beam angle of the evaluation diffraction peak; evaluating crystallographic quality of the SOI layer treated by the manufacturing process from the X-ray topograph; and repeating the method, including: modifying process conditions of the manufacturing process when a reference criterion for the crystallographic quality is unsatisfied; performing a second manufacturing process with the modified process conditions on a second SOI substrate having another SOI layer; and evaluating the crystallographic quality of the second SOI layer from a newly observed X-ray topograph, until the reference criterion for the crystallographic quality is satisfied.

DETAILED DESCRIPTION OF THE INVENTION

Figure 1:
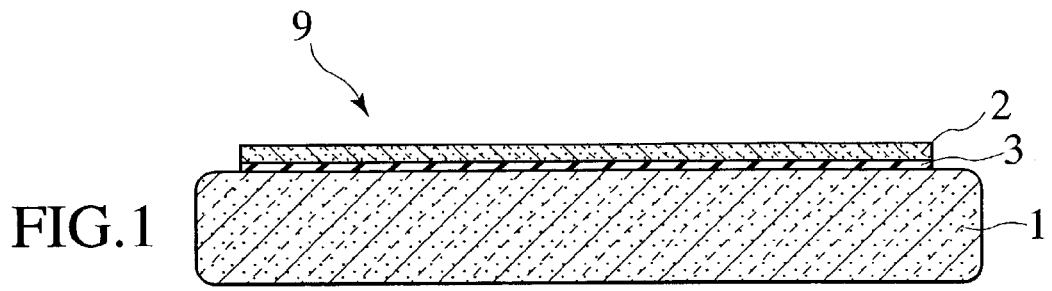
FIG. 1 is a cross-sectional view of a SOI substrate.

Various embodiments of the present invention will be described with reference to the accompanying drawings. It is to be noted that the same or similar reference numerals are applied to the same or similar parts and elements throughout the drawings, and the description of the same or similar parts and elements will be omitted or simplified.

First Embodiment

An SOI substrate 9 according to a first embodiment of the present invention includes, as shown in FIG. 1, a base substrate 1, which is a semiconductor substrate such as a silicon (Si) substrate; an SOI layer 2 provided on the base substrate 1 and serves as a semiconductor layer for an active region of a semiconductor device; and an insulating film layer 3 such as a silicon oxide ($SiO_2$) film or the like which is provided between the base substrate 1 and the SOI layer 2. Surface areas of the SOI layer 2 and the insulating film layer 3 are smaller than a surface area of the base substrate 1. As a result, a front surface of the base substrate 1 is exposed in an approximately 5 mm wide circumferential portion extending from the outer edge of the base substrate 1.

An example of a manufacturing method for a bonded SOI substrate is described in accordance with cross-sectional process diagrams shown in FIG. 2A through FIG. 2E.

Figure 2A:
FIGS. 2A through 2E are cross-sectional diagrams describing the manufacturing process of the SOI substrate.

(a) To begin with, as shown in FIG. 2A, a single-crystal silicon semiconductor substrate used as a base substrate 1 is prepared.

Figure 2B:
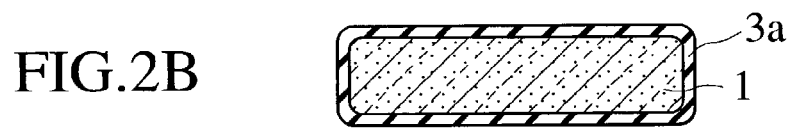

(b) A surface of the base substrate 1 is thermally oxidized, and as shown in FIG. 2B, an insulating film 3a of $SiO_2$ film is formed on the entire surface of the base substrate 1.

Figure 2C:
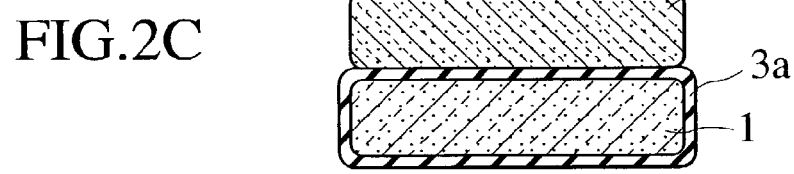

(c) Next, a semiconductor substrate 2a of another single-crystal silicon is overlaid onto the base substrate 1 that is covered with the insulating film 3a. Then, as shown in FIG. 2C, the semiconductor substrate 2a and the base substrate 1 are mated with facing surface to surface, and annealed so as to be bonded.

Figure 2D:
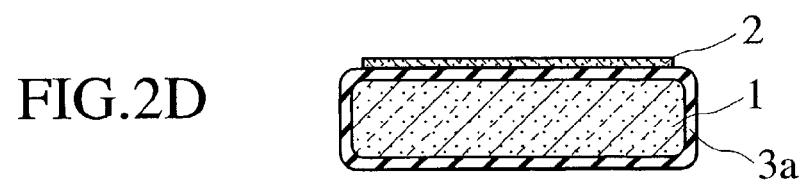

(d) Following bonding, the semiconductor substrate 2a is decreased in thickness by grinding and mirror-polishing processing, and as shown in FIG. 2D, an SOI layer 2 is formed.

Figure 2E:
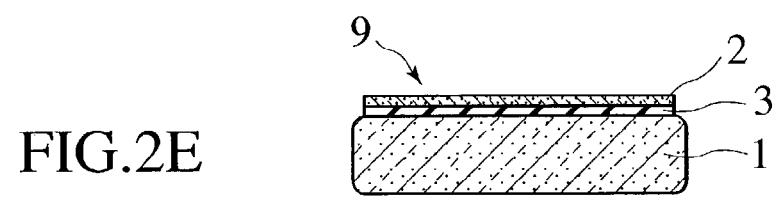

(e) Thereafter, the insulating film 3a exposed on the surface of the base substrate 1 is etched off, and as shown in FIG. 2E, an insulating film 3 remains after the etching and an SOI substrate 9 is fabricated.

A combination of grinding and polishing may be used as the thinning and mirror-polishing processing for the semiconductor substrate 2a. In addition, the thin SOI layer 2 may be obtained by flaking off an extra layer of the semiconductor substrate 2a, which is ion implanted with hydrogen or treated by an anodic oxidation process.

Figure 3:
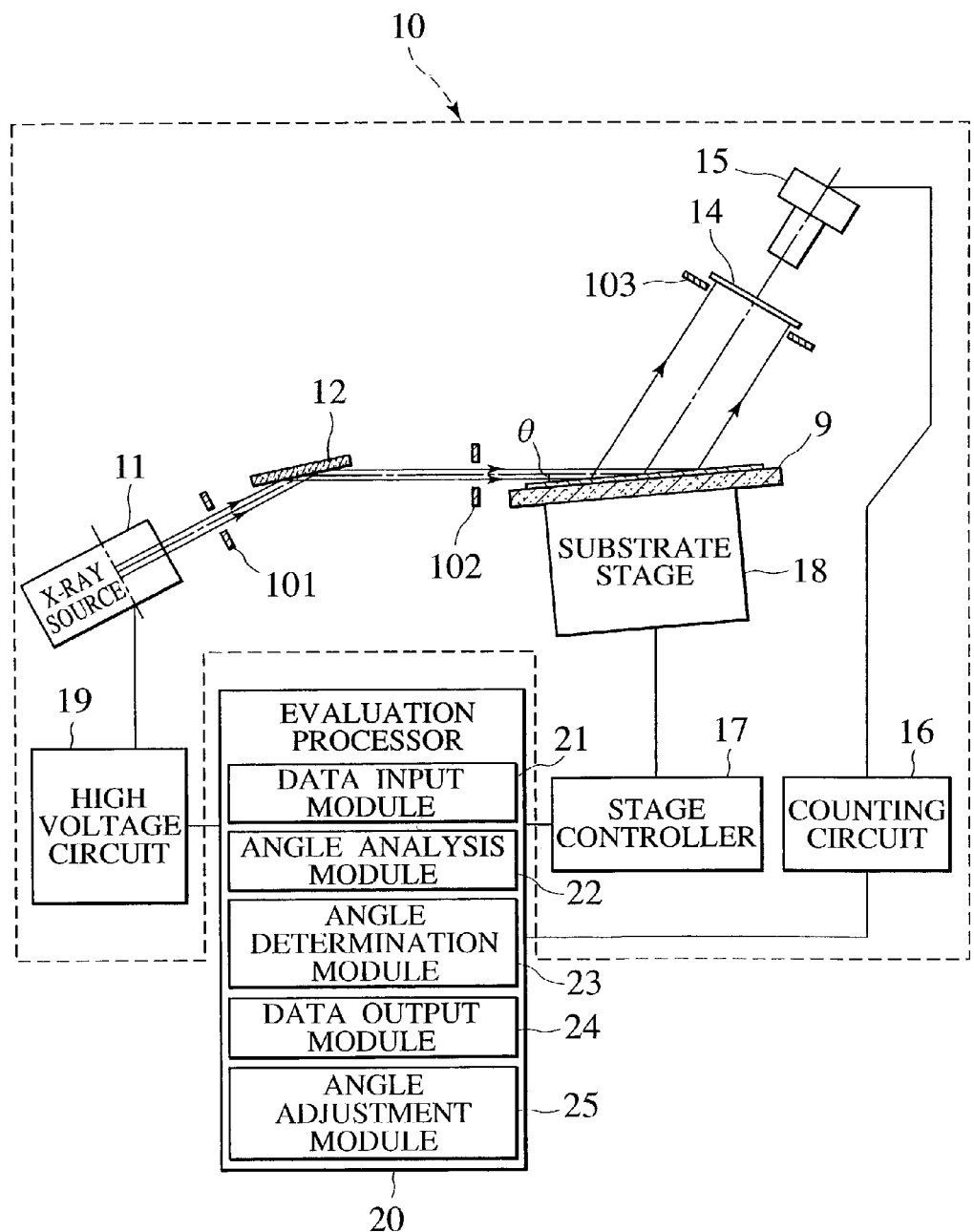
FIG. 3 is a schematic block diagram of a crystal evaluation apparatus according to a first embodiment of the present invention.

The crystal evaluation apparatus according to the first embodiment of the present invention includes, as shown in FIG. 3, an X-ray topography apparatus 10 and an evaluation processor 20.

Figure 4:
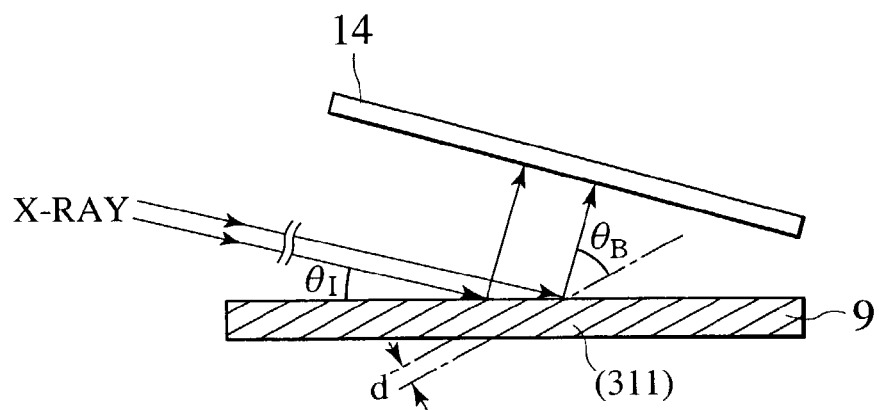
FIG. 4 is a diagram for describing a reflective configuration for X-ray topography according to the first embodiment of the present invention.

The X-ray topography apparatus 10 includes an X-ray source 11 generating X-rays by applying a high voltage from a high voltage circuit 19; a first slit 101 collimating the X-ray; a single crystal monochromator 12 reflecting the collimated X-ray beam with, for example a diffraction plane (111); a second slit 102 controlling the surface area of the reflected X-ray beam to irradiate a bonded SOI substrate 9; a substrate stage 18 for controlling the location and angle of the SOI substrate 9 by a stage controller 17; a third slit 103 controlling the detection surface area of the diffracted X-ray beam from the SOI substrate 9; an X-ray film 14 that captures the topograph from the diffracted X-ray beam; and a detector 15 such as a scintillation counter or the like, detecting the diffracted X-ray beam connected to a counting circuit 16. In the first embodiment of the present invention, as shown in FIG. 4, a reflective configuration is used where X-rays are incident on the front surface of the SOI substrate 9 with a shallow angle, and the reflected diffracted X-ray beam is measured. With the X-ray topography, using the diffraction effect of the X-ray, the localized distribution and shape of the defects and deformations included in the crystal may be observed. In addition, the X-ray topography is a non-destructive testing method and is suitable for tracking changes in the crystallographic quality due to thermal or mechanical processing of the semiconductor device manufacturing process.

The evaluation processor 20 configured to observe the X-ray topograph and evaluate the crystallographic quality of an SOI substrate, includes a data input module 21 for obtaining distribution of the diffraction intensity for the incident angle of the X-ray beam through the counting circuit 16; an angle analysis module 22 analyzing the incident beam angle corresponding to the diffraction intensity peak; an angle determination module 23 determining the incident beam angle corresponding to the base substrate 1 and the SOI layer of the SOI substrate 9; a data output module 24 outputting the determined incident beam angle to the stage controller 17; and an angle adjustment module 25 adjusting the output incident beam angle so that the diffracted X-ray intensity may be maximized near the output incident beam angle. The evaluation processor 20 may be constituted by a central processing unit (CPU) of a computer or the like.

A thermionic type X-ray tube is used for the X-ray source 11. The X-ray tube is used by isolating a $K_\alpha$ beam of the characteristic X-ray generated from a metal target of the X-ray tube by use of a filter. The $K_\alpha$ beam includes a $K_{\alpha 1}$ beam and $K_{\alpha 2}$ beam having neighboring wavelengths. Since isolation of the $K_{\alpha 1}$ and $K_{\alpha 2}$ beams is difficult, the $K_{\alpha 1}$ and $K_{\alpha 2}$ beams are used together as the $K_\alpha$ beam. In the first embodiment, copper (Cu) is used as the metal target of the X-ray tube. The wavelengths of the copper $K_{\alpha 1}$ and $K_{\alpha 2}$ beams are 0.15406 nm and 0.15444 nm, respectively.

In order for the X-ray beam to have a mirror reflection with the lattice plane of a crystal and diffract, the Bragg condition is required as shown in the following expression:

$$2*d*\sin\theta_B = n*\lambda \quad (1)$$

where $\lambda$ is the wavelength of the X-ray, d is the distance between diffraction lattice planes, and $\theta_B$ is the Bragg angle formed by the diffracted X-ray beam and the atomic plane.

In the first embodiment of the present invention, the copper $K_{\alpha 1}$ beam is used as the X-ray beam. With the reflective configuration, for example as shown in FIG. 4, given the diffraction plane of the SOI substrate 9 with a (100) orientation as the lattice plane (311), the Bragg angle $\theta_B$ is 28.07 degrees. The Bragg incident angle $\theta_1$ to the (100) plane of the SOI substrate 9 is 2.83 degrees. With X-ray topography observation using the reflective configuration, since the incident angle of the X-ray which satisfies the Bragg condition is shallow, it is possible to reflect the diffracted X-ray from a wide surface area of the SOI substrate 9 to the X-ray film 14 during a single X-ray exposure.

Figure 5:
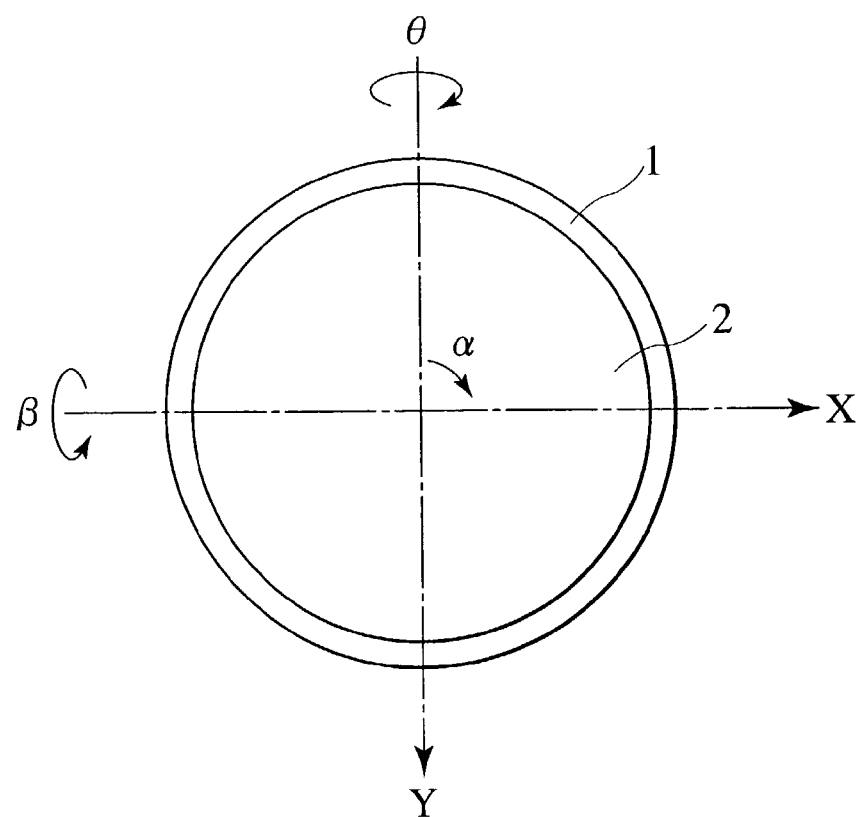
FIG. 5 is a diagram for describing the incident angle, rotation angle, and tilt angle adjusted with an X-ray topography apparatus of the present invention.

Normally, even if the X-ray is irradiated to a semiconductor substrate surface having a (100) orientation with an incident angle $\theta_1$ of 2.83 degrees, it is possible the diffracted X-ray from the diffraction plane (311) will not be observed. Due to machine errors, the actual planar orientation of the semiconductor substrate may deviate slightly from the (100) plane. Accordingly, before X-ray topography observation, an actual incident angle $\theta$ for the diffraction plane (311) must be precisely determined. In order to determine the incident angle $\theta$, the curve of the diffraction intensity (hereinafter, also referred to as a "rocking curve") is measured while rotating the SOI substrate 9 with a tri-axial stepper motor or the like attached to the substrate stage 18 of the X-ray topography apparatus 10. The incident angle $\theta$ corresponding to the Bragg condition is then determined from the location of a peak in the rocking curve. Imposing the x-y rectangular coordinates on the front surface of the SOI substrate 9 as shown in FIG. 5, in the case where the X-ray beam is incident along the x-axis, the incident angle $\theta$ is adjusted through an angle around the y-axis. In addition, a rotation angle around an axis perpendicular to the front surface of the SOI substrate 9 is given as $\alpha$, and a tilt angle around the x-axis is given as $\beta$. The incident angle $\theta$, the rotation angle $\alpha$, the tilt angle $\beta$, and horizontal shift in the x-y plane are automatically controlled by the stage controller 17. During measurement of the rocking curve, the X-ray film 14 is removed and the intensity of the diffracted X-ray beam is measured with the detector 15. To begin with, the incident angle of the X-ray beam $\theta$ on the SOI substrate 9 that is loaded on the substrate stage 18 is set at the Bragg incident angle $\theta_1$ of 2.83. The incident angle $\theta$, the rotation angle $\alpha$, and the tilt angle $\beta$, are then adjusted so as to maximize the intensity of the diffracted X-ray beam. Then, while maintaining the rotation angle $\alpha$ and the tilt angle $\beta$ fixed, the incident angle $\theta$ is yawed within a range of ±0.5 degrees from the angle that provides maximum intensity in order to obtain the rocking curve.

Figure 6:
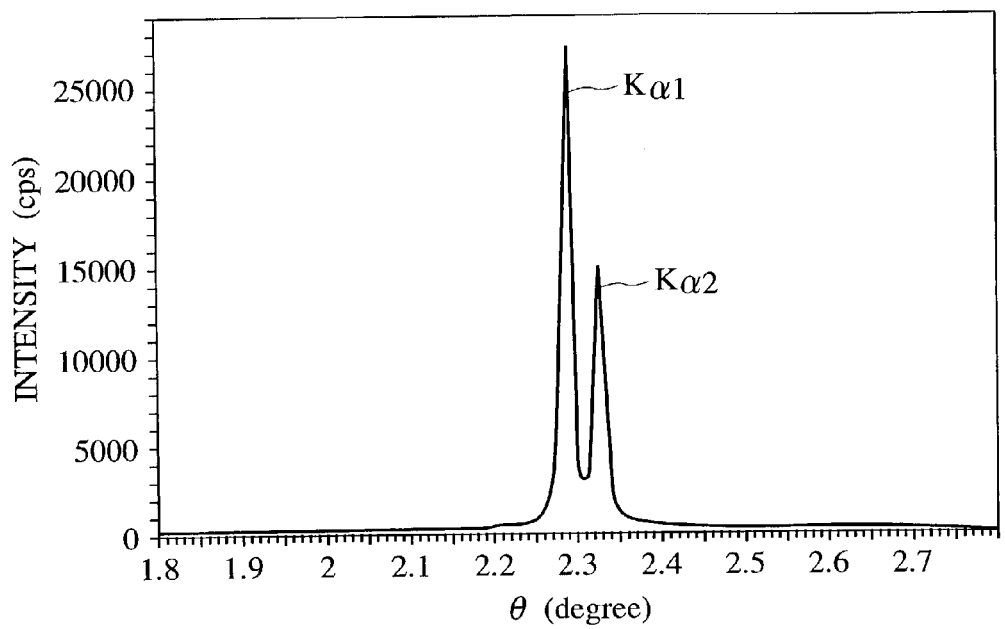
FIG. 6 is a graph showing a first rocking curve measured from the base substrate of the SOI substrate according to the first embodiment of the present invention.

With the evaluation method for a SOI substrate 9 according to the first embodiment of the present invention, to begin with, the rocking curves are measured for the front surfaces of the base substrate 1 and the SOI layer 2 of the SOI substrate 9. For instance, in the first embodiment of the present invention, for the bonded SOI substrate 9 with a (100) orientation and a 200 mm diameter, the thickness of the SOI layer 2 is 0.1 $\mu$m and the thickness of the insulating film layer 3 is 0.2 $\mu$m. The SOI substrate 9 is annealed at 1100° C. for 20 sec. Measurement of the rocking curve for the front surface of the base substrate 1 is performed by narrowing the second slit 102 of the X-ray topography apparatus 10 so as to irradiate the X-ray beam selectively on the approximately 5 mm wide exposed circumferential portion of the front surface of the base substrate 1 extending from the outer edge of the base substrate 1. From the measured rocking curve, as shown in FIG. 6, the peak of the diffracted X-ray due to the copper $K_{\alpha 1}$ beam is determined to be at the incident angle $\theta$ of 2.28 degrees. In addition, in FIG. 6, the diffraction intensity peak due to the $K_{\alpha 2}$ beam may also be determined in addition to the diffraction intensity peak from the $K_{\alpha 1}$ beam. However, only the $K_{\alpha 1}$ beam is used in this X-ray topography observation.

Figure 7:
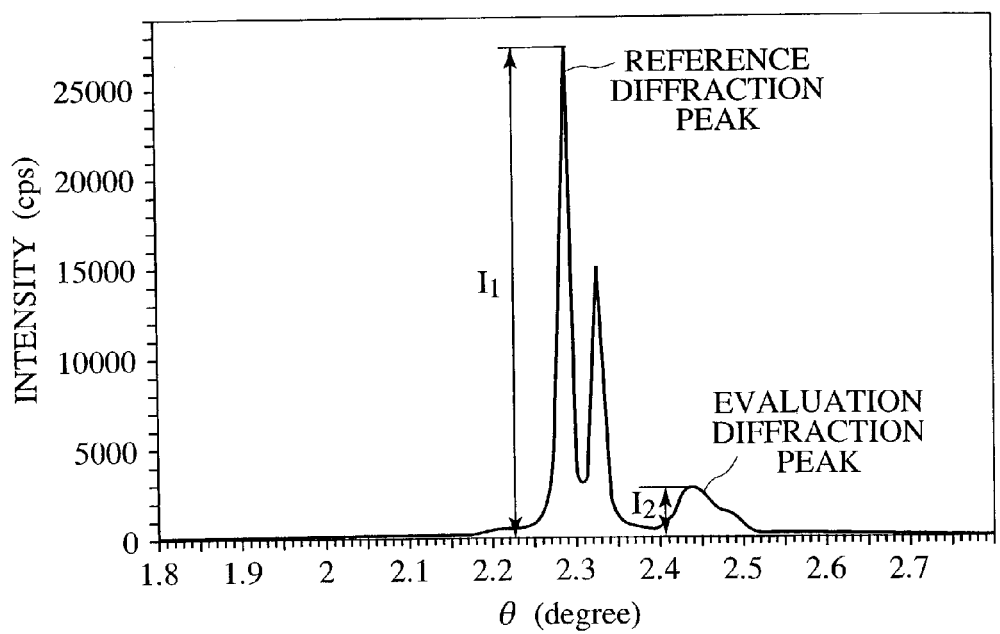
FIG. 7 is a graph showing a second rocking curve measured from the SOI layer of the SOI substrate according to the first embodiment of the present invention.

Next, making the second slit 102 approximately 35 mm wide, the substrate stage 18 is horizontally shifted to direct the X-ray beam to be incident on the center portion of the SOI substrate 9. Rocking curve measurement for the SOI layer 2 is then carried out without changing either the rotation angle $\alpha$ or the tilt angle $\beta$. In the measured rocking curve, a first diffraction intensity peak at diffraction intensity I1 and a second diffraction intensity peak at diffraction intensity I2 are seen at a first incident beam angle θ1 of 2.28 degrees and second incident beam angle θ2 of 2.43 degrees, respectively (see FIG. 7). The relationship between the respective locations of the first incident beam angle θ1 and the second incident beam angle θ2 changes depending on the deviation of the crystal axis between the base substrate 1 and SOI layer 2. Accordingly, there may also be cases where the second incident beam angle θ2 is smaller than the first incident angle beam θ1.

By comparing rocking curves obtained through the measurement of the base substrate 1 and the SOI layer 2, it is determined that the first peak is the diffracted X-ray beam of the base substrate 1. Accordingly, it is determined that the first incident beam angle θ1 and the second incident beam angle θ2 are incident angles satisfying the respective Bragg condition of the base substrate 1 and SOI layer 2 of the SOI substrate 9.

Figure 8:
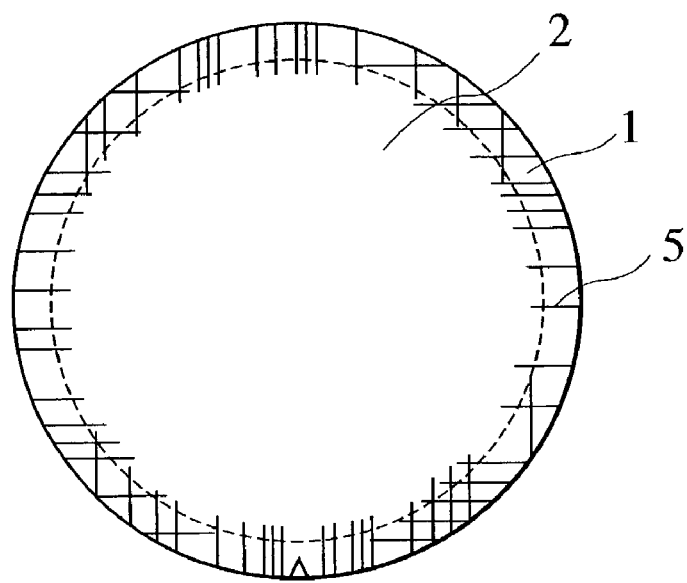
FIG. 8 is an illustration showing an X-ray topograph observed with the first incident angle for the SOI substrate according to the first embodiment of the present invention.
Figure 9:
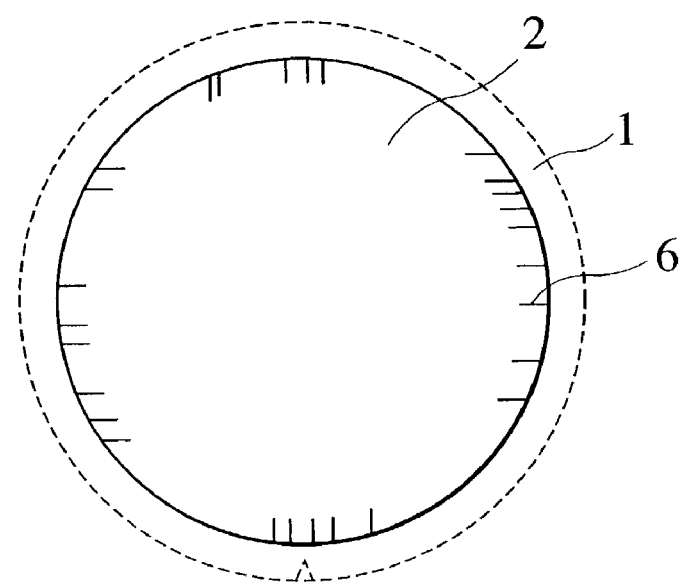
FIG. 9 is a illustration showing an X-ray topograph observed with the second incident angle for the SOI substrate according to the first embodiment of the present invention.

Thereinafter, the incident angle θ of substrate stage 18 is set to the first incident beam angle θ1 or the second incident beam angle θ2. Moreover, in order to correct the deviation in angle due to bowing or the like of the substrate, the rotation angle α, the tilt angle β, and the incident θ are finely adjusted before the X-ray topography observation. With the X-ray topograph observed at the first incident beam angle θ1, as shown in FIG. 8, it is determined that many dislocations 5 have been induced around the outer region of the base substrate 1. In addition, with the X-ray topograph observed at the second incident beam angle θ2, as shown in FIG. 9, it is determined that dislocations 6 have been induced around the outer region of the SOI layer 2. The locations and densities of the dislocations 5 and dislocations 6 are different from each other, and the dislocations 5 and dislocations 6 are determined as showing the respective crystal defects in the base substrate 1 and the SOI layer 2. It should be noted that in FIG. 8 and FIG. 9, description has been made using dislocations to show the crystal defects, however, stacking faults, twin crystal planes, impurity segregations, oxide precipitations, and the like may also be observed with, for instance, changes in the diffraction pattern or diffraction intensity of the X-ray topograph. Thus, the crystal qualities of the base substrate 1 and the SOI layer 2 may be separately evaluated.

Figure 10:
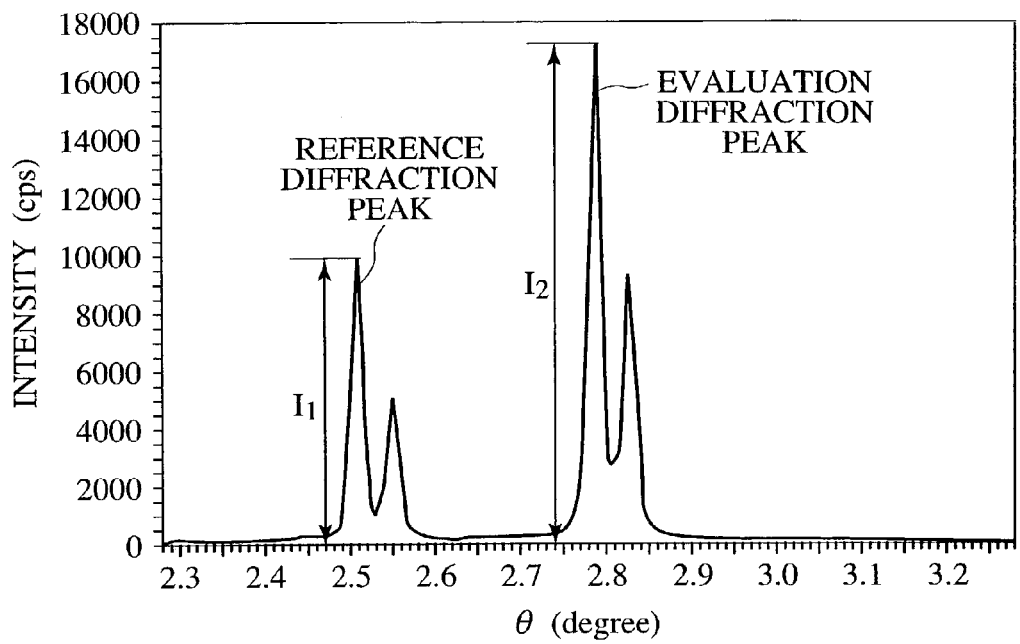
FIG. 10 is a graph showing another example of a second rocking curve measured from the SOI layer of the SOI substrate according to the first embodiment of the present invention.
Figure 11:
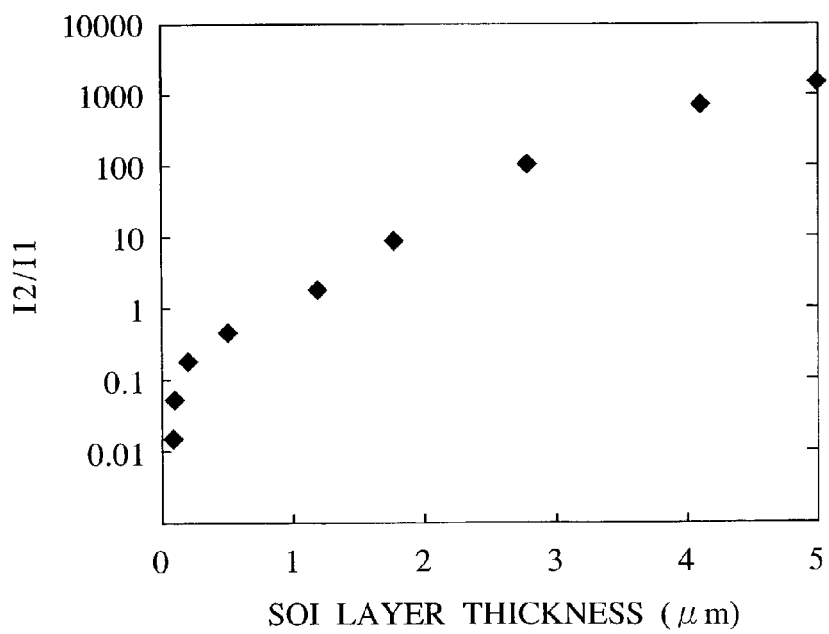
FIG. 11 is a graph showing the relationship between the SOI layer thickness and peak intensity ratio obtained with the rocking curve through the reflective configuration according to the first embodiment of the present invention.

Rocking curve measurement has been further carried out with a change in the thickness of the SOI layer 2 to a range of between approximately 0.1 and 5 μm. For example, with an SOI substrate 9 having an SOI layer 2 with a thickness of 1.2 μm, as shown in FIG. 10, a first incident beam angle θ1 of 2.51 degrees and a second incident beam angle θ2 of 2.79 degrees was seen for the first diffraction intensity peak and second diffraction intensity peak, respectively. Since the thickness of the SOI layer 2 has been increased to 1.2 μm in comparison with the case in FIG. 7 where the thickness of the SOI layer 2 is 0.1 μm, the diffraction intensity I2 of the second diffraction intensity peak is larger. The diffraction intensity ratio I2/I1 of the second diffraction intensity peak to the first diffraction intensity peak, as shown in FIG. 11, increases as the SOI layer 2 becomes thicker. When the thickness of the SOI layer 2 is 5 μm or greater, the diffraction intensity I1 becomes equal to or less than the background level, and the first diffraction intensity peak is impossible to detect. Accordingly, when the diffraction intensity ratio I2/I1 is in a range of about 0.01 and 1000, it is possible to evaluate crystallographic quality across all regions throughout the thickness of the SOI layer 2.

When the thickness of the SOI layer 2 of the SOI substrate 9 is 5 μm or greater, the diffraction plane may be changed to a lattice plane (422) or (511) instead of a lattice plane (311). In the case where the diffraction plane (422) or (511), the Bragg incident angle θ1 goes to 8.76 degrees or 31.69 degrees, and the detected thickness is either approximately 10 μm or approximately 30 μm. Thus, by changing the diffraction plane, it is possible to observe even for thick SOI layers 2. In addition, by increasing the incident X-ray intensity or the resolution, it may be possible to observe the diffracted X-ray for the SOI layer 2 below 0.1 μm. In addition, when the observation is carried out for a plurality of diffraction planes, it is also possible to examine the distribution of crystal defects along the thickness of the SOI layer 2. It should be noted that even if the diffraction plane is changed, the detectable diffraction intensity ratios I2/I1 for first and second peaks still ranges between 0.01 and 1000, as with the case where the lattice plane (311).

Figure 12:
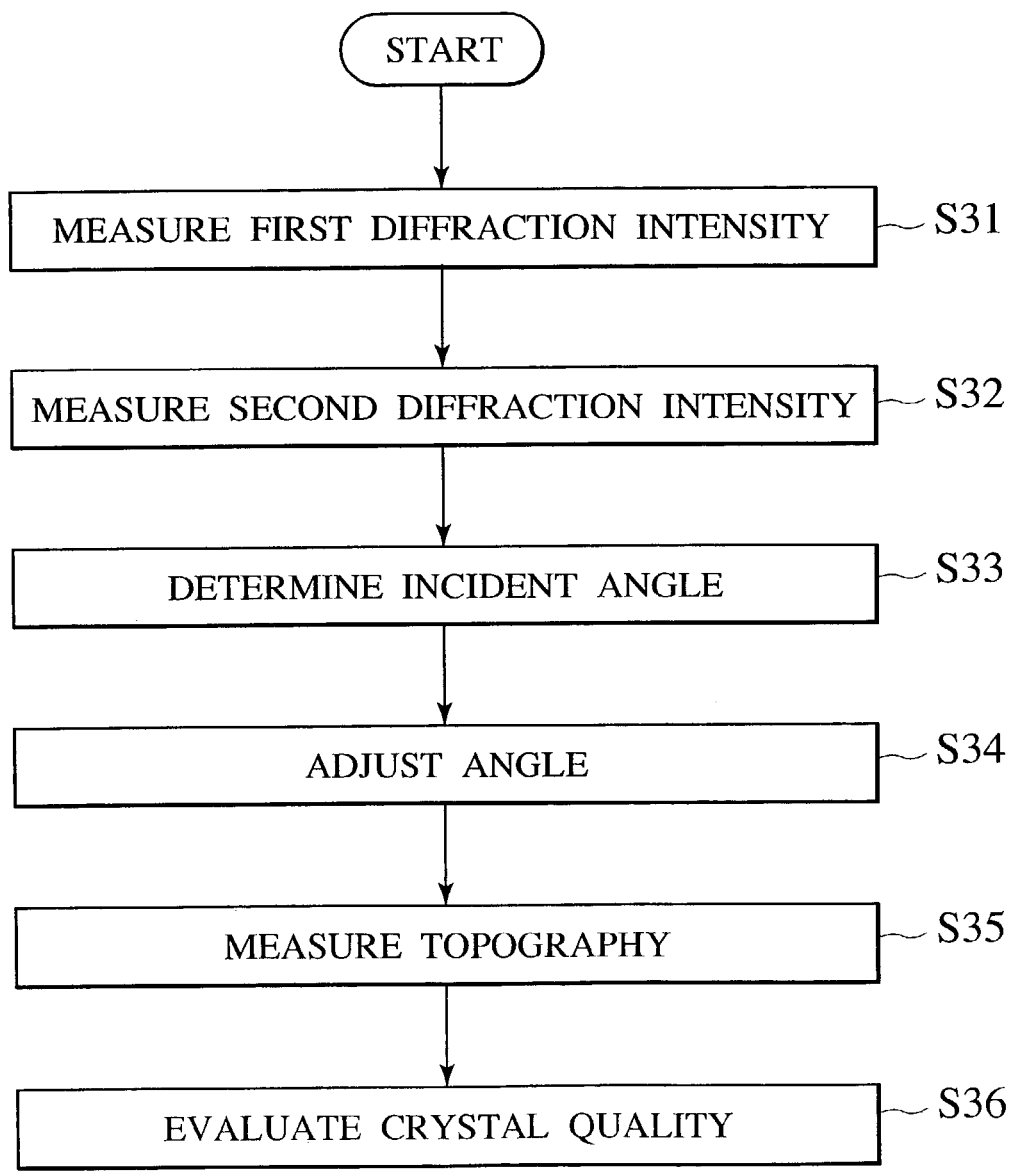
FIG. 12 is a flowchart for describing an evaluation method of the SOI substrate according to the first embodiment of the present invention.

Next, an evaluation method for the SOI substrate 9 according to the first embodiment of the present invention is described using the flowchart shown in FIG. 12.

(a) To begin with, a bonded SOI substrate 9 with a (100) orientation and diameter of 200 mm is loaded on the substrate stage 18 of the X-ray topography apparatus 10. In step S31, an X-ray beam is irradiated selectively toward the circumferential portion of the SOI substrate 9 where the base substrate 1 is exposed, and a first rocking curve is measured using the detector 15. The data for the first rocking curve is transmitted from the counting circuit 16 to the data input module 21 of the evaluation processor 20.

(b) Next, the SOI substrate 9 is shifted so as to define the X-ray irradiation location at the center of the substrate by controlling the substrate stage 18 with the stage controller 17. In step S32, without changing either the rotation angle α or the tilt angle β, a second rocking curve is measured using the detector 15. The data for the second rocking curve is transmitted from the counting circuit 16 to the data input module 21 of the evaluation processor 20.

(c) The angle analysis module 22 receives the first and second rocking curve data from the data input module 21 and determines the incident angle at the location of the diffraction intensity peak. In step S33, the angle determination module 23 determines the first incident beam angle θ1 of the base substrate 1 and the second incident beam angle θ2 of the SOI layer 2 from the incident angle determined by the angle analysis module 22.

(d) The data output module 24 outputs the second incident beam angle θ2 determined by the angle determination module 23 to the stage controller 17 and sets the incident θ of the substrate to the second incident beam angle θ2. In step S34, the angle adjustment module 25 finely adjusts and sets the rotation angle α, the tilt angle β, and the incident θ so as to maximize the X-ray diffraction intensity.

(e) X-ray film is loaded, and in step S35, the X-ray topography observation is performed.

(f) In step S36, the crystallographic quality of the SOI layer 2 is evaluated based on the observed X-ray topograph data by comparing the data to a reference criterion.

When applying the crystal evaluation method according to the first embodiment of the present invention to a semiconductor device manufacturing process, data from an X-ray topograph observed prior to a process such as thermal processing or the like, where the crystal defects can be induced, may serve as the reference criterion. Since the diffraction intensity and diffraction pattern of the X-ray topograph changes due to the crystal defects, it is possible to determine whether or not the crystal defects are induced during the semiconductor device manufacturing process. In addition, with the first embodiment of the present invention, the first rocking curve of the base substrate 1 is measured first, however, measurement of the second rocking curve of the SOI layer 2 may naturally be performed first.

As the SOI layer 2 of the SOI substrate 9 decreases in thickness to approximately 0.1 $\mu$m, the diffracted X-ray intensity becomes smaller. Then, change in the diffraction intensity or the diffraction pattern of the observed X-ray topograph may become difficult to determine. In such a case, by returning to step S34, the incident angle may be set to the first incident beam angle θ1 to perform the X-ray topography observation for the base substrate 1. By referencing the crystal evaluation of the base substrate 1, the crystallographic quality of the SOI layer 2 may be estimated.

Figure 13:
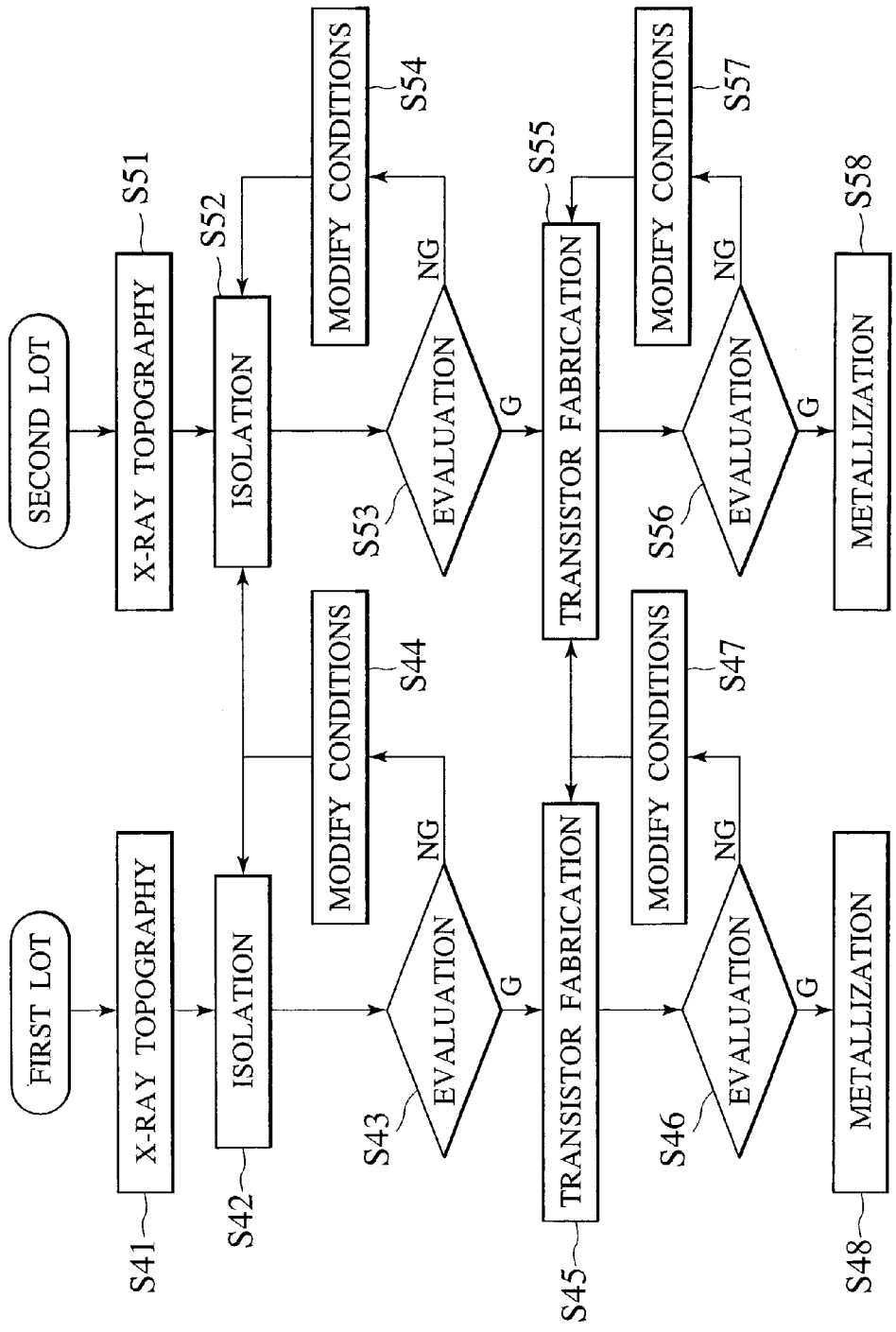
FIG. 13 is a flowchart for describing a semiconductor device manufacturing method using the evaluation method of the SOI substrate according to the first embodiment of the present invention.

Next, a semiconductor device manufacturing method using the evaluation method for the SOI substrate 9 according to the first embodiment of the present invention is described using the flowchart shown in FIG. 13. The semiconductor device is manufactured using the SOI substrate 9 formed by the bonding method. Taking twenty or so SOI substrates 9 as one lot, the semiconductor device manufacturing process proceeds sequentially in the order of first lot, second lot, and so forth. Here, Letters "G" and "NG" in steps S43, S46, S53, and S56, are defined as follows: the letter "G" means that generation of crystal defects is not found, and the letter "NG" means that generation of crystal defects is found.

(a) To begin with, in step S41, several SOI substrates 9 of the first lot are sampled, and the X-ray topography observation for the SOI layer 2 and the base substrate 1 is carried out.

(b) In step S42, using one of the SOI substrates 9 on which the X-ray topography observation has been performed, an element isolation process is performed, preceding the other SOI substrate in the same lot. Then, in step S43, the X-ray topography observation is performed for the SOI layer 2 on which the isolation regions have been formed, and the evaluation is performed as to whether or not the crystal defects have been induced. It should be noted that the X-ray topography observation results for the base substrate 1 may be used as reference data for the evaluation of the SOI layer 2.

(c) When generation of crystal defects is found in the results of evaluating the SOI layer 2 on which the isolation regions have been formed, in step S44, the element isolation process conditions are modified. Then, using another one of the SOI substrates 9 on which the X-ray topography observation has been performed, in step S42, an element isolation process is performed with the modified element isolation process conditions. Then, in step S43, the evaluation of a SOI layer 2 of the another one of the SOI substrates 9 is performed.

(d) When generation of crystal defects in the SOI layer 2 is not found in the results of evaluating the SOI layer 2 on which the isolation regions have been formed, in step S45, transistors or the like, are fabricated in the isolation regions of the SOI layer 2. Then, in step S46, the X-ray topography observation is performed for the SOI layer 2 on which the transistors or the like have been fabricated, and the evaluation is performed as to whether or not the crystal defects have been induced. It should be noted that the X-ray topography observation results for the base substrate 1 may be used as reference data for the evaluation of the SOI layer 2.

(e) When generation of the crystal defects is found in the results of evaluating the SOI layer 2 on which the transistors or the like have been fabricated, in step S47, the transistor fabrication process conditions are modified. Then, using a SOI substrate 9 on which the element isolation process of step S42 and the evaluation of step S43 have been performed, in step S45, the transistor fabrication process is performed with the modified transistor fabrication process conditions. Then, in step S46, the evaluation of the SOI layer 2 is carried out.

(f) When generation of the crystal defects in the SOI layer 2 is not found in the results of evaluating the SOI layer 2 on which the transistors or the like have been newly fabricated, in step S48, an interconnect formation process is carried out on the front surface of the SOI layer 2 where the transistors or the like have been fabricated. Thereafter, semiconductor device manufacturing is implemented under the newly set process conditions for the rest of the SOI substrates 9 in the first lot.

(g) Next, in step S51, several SOI substrates 9 of the second lot are sampled, and the X-ray topography observation for the SOI layer 2 and the base substrate 1 is carried out.

(h) In step S52, using one of the SOI substrates 9 on which the X-ray topography observation has been performed, an element isolation process is performed preceding processing of the other SOI substrate in the same lot and in step S53, the SOI layer 2 on which element isolation regions have been formed is evaluated. It should be noted that the element isolation process is performed under the conditions modified with the first lot.

(i) When generation of the crystal defects is found in the results of evaluating the SOI layer 2 on which the element isolation regions have been formed, in step S54, the element isolation process conditions are modified. Then, using another SOI substrate 9 on which the X-ray topography observation has been performed, in step S52, the element isolation process is performed with the modified element isolation process conditions. Then, in step S53, the evaluation of the SOI layer 2 is performed.

(j) When generation of the crystal defects in the SOI layer 2 is not found in the results of evaluating the SOI layer 2 on which the element isolation regions have been formed, in step S55, transistors or the like are fabricated in the element isolation regions of the SOI layer 2, and in step S56, the SOI layer 2 on which the transistors or the like are fabricated are evaluated. It should be noted that the transistor fabrication process is performed under the conditions modified with the first lot.

(k) When generation of the crystal defects is found in the results of evaluating the SOI layer 2 on which the transistors or the like have been fabricated, in step S57, the transistor fabrication process conditions are modified. Then, using the SOI substrate 9 on which the element isolation process of step S52 and the evaluation of step S53 have been performed, in step S55, the transistor fabrication process is performed with the modified transistor fabrication process conditions. Then, in step S56, the evaluation of the SOI layer 2 is performed.

(l) When generation of the crystal defects in the SOI layer 2 is not found in the results of evaluating the SOI layer 2 on which the transistors or the like have been newly fabricated, in step S58, a metallization process is carried out so as to form interconnects on the front surface of the SOI layer 2 where the transistors or the like have been fabricated. In addition, semiconductor device manufacturing is implemented under the newly set process conditions for rest of the SOI substrates 9 in the second lot. Moreover, the semiconductor device manufacturing processes for new lots are also implemented with the procedures described above.

With the semiconductor device manufacturing method according to the first embodiment of the present invention, since the evaluation of the crystallographic quality for the SOI layer 2 of the SOI substrate is possible at each step of the semiconductor device manufacturing process, it is now possible to effectively manufacture high quality semiconductor devices. With the semiconductor device manufacturing method described above, the evaluation of the SOI layer 2 was carried out following the element isolation process and the transistor fabrication process, however, the evaluation may naturally be carried out following the thermal treatment processing or the mechanical treatment processing included in each process. For example, with the transistor fabrication process, the SOI layer 2 may be evaluated following annealing after an ion implantation process to fabricate the channel region or the source/drain region, or following processing such as reactive ion etching (RIE) of the polysilicon film during gate electrode formation.

Second Embodiment

Figure 14:
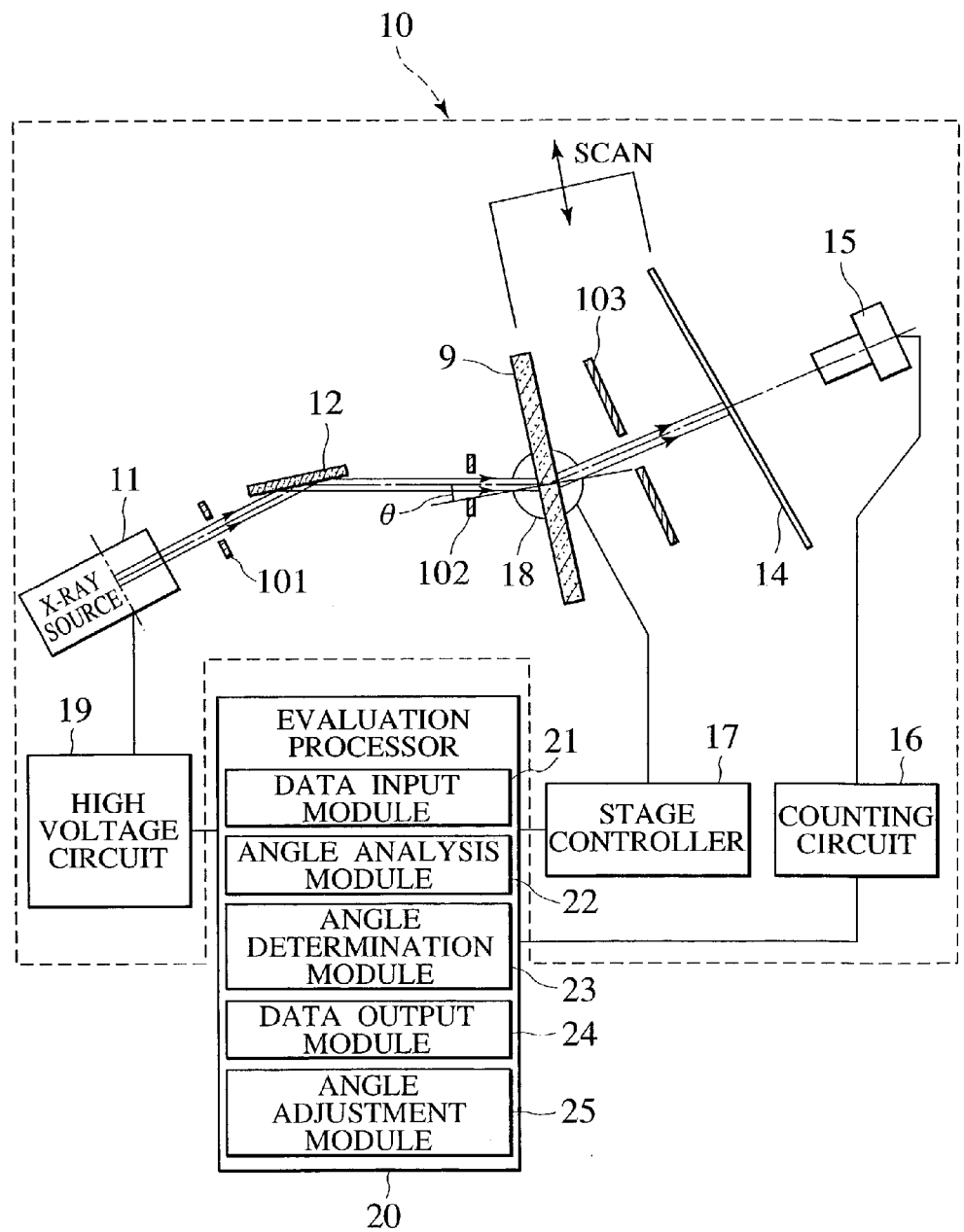
FIG. 14 is a schematic block diagram of a crystal evaluation apparatus according to a second embodiment of the present invention.

In the evaluation method for an SOI substrate according to a second embodiment of the present invention, a transmissive configuration is used where X-rays are incident on a front surface of the SOI substrate 9, and the diffracted X-rays transmitted from the SOI substrate are observed. As shown in FIG. 14, a rear surface of the SOI substrate 9 is loaded onto the substrate stage 18 so as to face the third slit 103 of the X-ray topography apparatus 10. The third slit 103 defines narrowly the X-rays that arrive after passing through the SOI substrate 9 with an angle of the incident direction, and to allow only the diffracted X-rays to be transmitted on the X-ray film. Therefore, with the X-ray topography observation, the stage controller 17 and the X-ray film 14 are synchronized to scan so as to allow the observed region of the SOI substrate 9 to be sequentially transmitted to the X-ray film 14. Since the evaluation method for the SOI substrate according to the second embodiment of the present invention is similar to the evaluation method for the SOI substrate of the first embodiment, except for the transmissive configuration, repetitive description is omitted.

Figure 15:
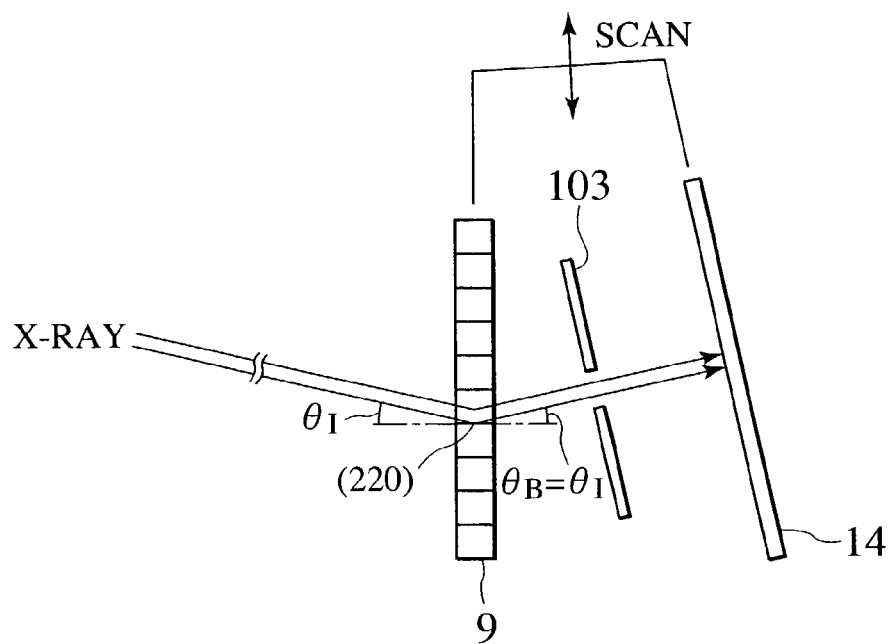
FIG. 15 is a diagram for describing a transmissive configuration for X-ray topography according to the second embodiment of the present invention.

In the second embodiment of the present invention, a molybdenum (Mo) $K_{\alpha 1}$ beam with a wavelength $\lambda$=0.07093 nm is used as the X-ray. With the transmissive configuration, for example as shown in FIG. 15, given the diffraction plane g of the SOI substrate 9 with a (100) orientation of the lattice plane (220), the Bragg angle $\theta_B$ is 10.65 degrees. In addition, with the transmissive configuration, the Bragg incident angle $\theta_I$ is 10.65 degrees, the same as the Bragg angle $\theta_B$. With the X-ray topography observation using the transmissive configuration, since the diffracted X-rays that have arrived after passing through the SOI substrate 9 are used, the SOI layer 2 may be evaluated throughout the entire thickness. The diffraction plane used with the transmissive configuration may, for example, be a lattice plane (004) or the like. When the diffraction plane (004), the Bragg angle $\theta_B$ is 15.14 degrees.

Figure 16:
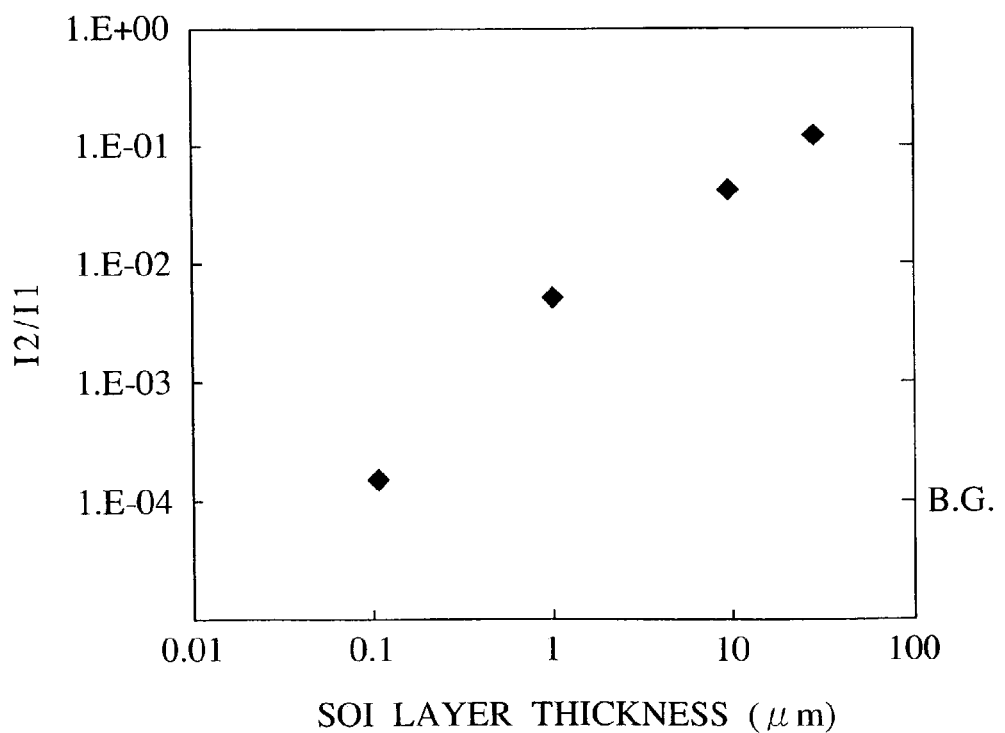
FIG. 16 is a graph showing the relationship between the SOI layer thickness and peak intensity ratio obtained with the rocking curve through the transmissive configuration according to the second embodiment of the present invention.

Using the evaluation method of the SOI layer 2 according to the second embodiment of the present invention, rocking curve measurement was carried out changing the thickness of the SOI layer 2 to range between approximately 0.1 and 30 $\mu$m. The diffraction intensity ratio I2/I1 of the diffracted X-ray of the SOI layer 2 to the diffracted X-ray of the base substrate 1, as shown in FIG. 16, increases as the SOI layer 2 becomes thicker. When the thickness of the SOI layer 2 is 0.1 $\mu$m or less, the diffraction intensity I2 of the SOI layer 2 is equal or less than the background level, and is impossible to detect. Accordingly, when diffraction intensity ratio I2/I1 ranges from approximately $10^{-4}$ and higher corresponding to the thickness of the SOI layer 2 being approximately 0.1 $\mu$m or greater, it is possible to evaluate crystallographic quality across all regions throughout the thickness of the SOI layer 2.

Other Embodiments

With the first and second embodiments of the present invention, an SOI substrate is used where the SOI layer 2 has a diameter that is approximately 10 mm smaller than the base substrate 1. However, a partial SOI substrate where the SOI layer is formed on one part of the region on the base substrate is naturally also permissible. With the partial SOI substrate, the non-SOI layer region is formed using an epitaxial layer grown on the base substrate. Accordingly, since the epitaxial layer is considered as having the same crystal orientation as the base substrate, the rocking curve of the base substrate may be measured from the epitaxial layer.

In addition, in the first and second embodiments of the present invention, description was made using a Cu or Mo $K_{\alpha 1}$ beam for the X-ray source, however, $K_{\alpha 1}$ beams of other metals such as silver (Ag), cobalt (Co), or iron (Fe), or an X-ray having an arbitrary wavelength using synchrotron radiation may naturally be permissible.

Furthermore, in the first and second embodiments of the present invention, incident $\theta$ of the X-ray was determined by the rocking curve, however, even without obtaining the rocking curve, the X-ray diffraction intensity may naturally be measured through images using an X-ray camera or an X-ray television.

Various modifications will become possible for those skilled in the art after receiving the teachings of the present disclosure without departing from the scope thereof.

What is claimed is:

1. A method for evaluating an SOI layer on an insulating film disposed on a base substrate so as to construct an SOI substrate, comprising:

measuring a first diffraction intensity distribution of an X-ray beam for an incident beam angle formed with the X-ray beam and a front surface of the SOI substrate by irradiating the X-ray beam onto a front surface of the base substrate;

measuring a second diffraction intensity distribution of the X-ray beam for the incident beam angle by irradiating the X-ray beam onto the front surface of the SOI substrate;

determining an evaluation diffraction peak corresponding to the SOI layer from the first and the second diffraction intensity distributions; and observing an X-ray topograph by irradiating the X-ray beam on the SOI layer with an incident beam angle of the evaluation diffraction peak, after adjusting a rotation angle around an axis perpendicular to the front surface of the SOI substrate, a tilt angle around a horizontal axis along an incident direction of the X-ray beam, and the incident beam angle of the evaluation diffraction peak.

2. The method of claim 1, further comprising:

determining a reference diffraction peak corresponding to the base substrate from the first diffraction intensity distribution;

observing a second X-ray topograph by irradiating the X-ray beam on the SOI layer with another incident beam angle of the reference diffraction peak; and evaluating the crystallographic quality of the base substrate using the second X-ray topograph.

3. The method of claim 2, wherein the second X-ray topograph is further observed after adjusting a rotation angle around an axis perpendicular to the front surface of the SOI substrate, a tilt angle around a horizontal axis along an incident direction of the X-ray beam, and the incident beam angle.

4. The method of claim 2, wherein a ratio of the evaluation diffraction peak to the reference diffraction peak is in a range of about $10^{-4}$ to $10^3$.

5. The method of claim 1, wherein a diffracted beam of the X-ray beam is transmitted from the front surface of the SOI substrate for observation.

6. The method of claim 1, wherein a diffracted beam of the X-ray beam is transmitted to a rear surface of the SOI substrate for observation.

7. An evaluation processor for an SOI layer on an insulating film disposed on a base substrate so as to construct an SOI substrate, comprising:
   an X-ray topography apparatus;
   a data input module configured to receive X-ray beam diffraction intensity data corresponding to the base substrate and the SOI layer observed by the X-ray topography apparatus;
   an angle analysis module configured to analyze an incident beam angle of a diffraction intensity peak from a distribution of the diffraction intensity data;
   an angle determination module configured to determine a first incident beam angle corresponding to the base substrate, and a second incident beam angle corresponding to the SOI layer from the analyzed incident beam angle;
   a data output module configured to output the first and second incident beam angles to the X-ray topography apparatus; and
   an angle adjustment module configured to determine adjustments to the evaluation processor based on a rotation angle around an axis perpendicular to a front surface of the SOI substrate, a tilt angle around a horizontal axis along an incident direction of an X-ray beam, and the incident beam angle of a diffraction intensity peak.

8. A method for manufacturing a semiconductor device, comprising:
   forming a first SOI layer on an insulating film disposed on a base substrate so as to construct a first SOI substrate;
   performing a first manufacturing process for forming a semiconductor device on the first SOI layer;
   observing a first X-ray topograph of the first SOI layer treated by the manufacturing process, comprising:
      measuring a first diffraction intensity distribution of an X-ray beam for an incident beam angle formed with the X-ray beam and a front surface of the first SOI substrate by irradiating the X-ray beam onto a front surface of the base substrate;
      measuring a second diffraction intensity distribution of the X-ray beam for the incident beam angle by irradiating the X-ray beam onto the front surface of the first SOI substrate;
      determining an evaluation diffraction peak corresponding to the first SOI layer from the first and the second diffraction intensity distributions; and
      observing the first X-ray topograph by irradiating the X-ray beam on the first SOI layer with an incident beam angle of the evaluation diffraction peak;
   evaluating a first crystallographic quality of the SOI layer treated by the manufacturing process from the first X-ray topograph; and
   repeating the following method, including:
      modifying process conditions of the manufacturing process when a reference criterion for the crystallographic quality is unsatisfied;
      performing a second manufacturing process with the modified process conditions on a second SOI substrate having a second SOI layer; and
      evaluating a second crystallographic quality of the second SOI layer from a newly observed X-ray topograph, until the reference criteria for the first and second crystallographic quality is satisfied.

9. The method of claim 8, wherein the first X-ray topograph and the newly observed X-ray topograph are further observed after adjusting a rotation angle around an axis perpendicular to the front surface of the first SOI substrate, a tilt angle around a horizontal axis along an incident direction of the X-ray beam, and the incident beam angle.

10. The method of claim 9, wherein the first manufacturing process and the second manufacturing process include at least one of an annealing process, an oxidization process, an ion implantation process, a plasma irradiation process, a crystal growth process, or a film deposition process.

11. The method of claim 8, further comprising:
   determining a reference diffraction peak corresponding to the base substrate from the first diffraction intensity distribution;
   observing another X-ray topograph by irradiating the X-ray beam on one of the first SOI layer and the second SOI layer with another incident beam angle of the reference diffraction peak; and
   evaluating a crystallographic quality of the base substrate with the another X-ray topograph.

12. The method of claim 11, wherein the another X-ray topograph is further observed after adjusting a rotation angle around an axis perpendicular to the front surface of the first SOI substrate, a tilt angle around a horizontal axis along an incident direction of the X-ray beam, and the incident beam angle.

13. The method of claim 11, wherein a ratio of the evaluation diffraction peak to the reference diffraction peak is in a range of about $10^{-4}$ to $10^3$.

14. The method of claim 8, wherein a diffracted beam of the X-ray beam is transmitted from the front surface of the first SOI substrate for observation.

15. The method of claim 8, wherein a diffracted beam of the X-ray beam is transmitted to a rear surface of the first SOI substrate for observation.

16. The method of claim 8, wherein the reference criterion is the crystallographic quality of the SOI layer determined prior to the first manufacturing process.

* * * * *